United States Patent [19]
Roost

[11] Patent Number: 5,186,062
[45] Date of Patent: Feb. 16, 1993

[54] METHOD OF INVESTIGATING THE GAIT OF A LIVING BEING

[75] Inventor: Walter Roost, Zurich, Switzerland

[73] Assignee: Standard St Sensortechnik Ag., Chur, Switzerland

[21] Appl. No.: 455,397

[22] PCT Filed: May 18, 1989

[86] PCT No.: PCT/CH89/00092
§ 371 Date: Mar. 30, 1990
§ 102(e) Date: Mar. 30, 1990

[87] PCT Pub. No.: WO89/11246
PCT Pub. Date: Nov. 30, 1989

[30] Foreign Application Priority Data
May 19, 1988 [DE] Fed. Rep. of Germany ....... 3817095

[51] Int. Cl.$^5$ ............................ A61B 5/11; G01L 5/16; G01L 5/00
[52] U.S. Cl. .................................... 73/865.4; 128/779; 128/782; 128/379.08; 73/862.041
[58] Field of Search ............ 73/865.4, 862.04, 862.64, 73/862.65, 862.66, 862.67, 380, 381, 379; 128/779, 782

[56] References Cited

U.S. PATENT DOCUMENTS

| | | | |
|---|---|---|---|
| 3,090,226 | 5/1963 | Corti et al. | 73/862.64 |
| 3,340,726 | 9/1967 | Armstrong et al. | 73/570 |
| 3,894,437 | 7/1975 | Hagy et al. | 73/865.4 |
| 3,906,931 | 9/1975 | Terckov | 73/862.04 |
| 4,023,634 | 5/1977 | Provi et al. | 73/862.65 X |
| 4,195,643 | 4/1980 | Pratt, Jr. | 128/779 |
| 4,233,845 | 11/1980 | Pratt, Jr. | 73/865.4 |
| 4,267,728 | 5/1981 | Manley et al. | 73/172 |
| 4,411,327 | 10/1983 | Lockery et al. | 177/DIG. 9 X |

FOREIGN PATENT DOCUMENTS

| | | | |
|---|---|---|---|
| 65176 | 11/1982 | European Pat. Off. | |
| 3212660 | 10/1983 | Fed. Rep. of Germany | 73/862.04 |
| 3214306 | 10/1983 | Fed. Rep. of Germany | 73/862.04 |
| 42025 | 2/1987 | Japan | 73/862.04 |
| 2155555 | 9/1983 | United Kingdom | 73/862.04 |

OTHER PUBLICATIONS

"A Method of Measuring the Temporal/Distance Factors of Gait", *Proceedings of the Conference on the Applications of Electronics in Medicine Southampton, England 6–8, Apr. 1976*, Dr. J. C. Wall et al., pp. 341–350.

"A Gait Analyzer/Trainer Instrumentation System", *J. Biomechanics* vol. 12, No. 7, pp. 543–549, pub. 1979, R. H. Gabel et al.

"Electronic Measurement of Instantneons Foot-Floor Contact Pattern During Gair", *J. Biomechanics*, vol. 13, No. 10, pp. 875–880, pub. 1980, L. F. Draganich et al.

*Primary Examiner*—Tom Noland
*Attorney, Agent, or Firm*—EGLI International

[57] ABSTRACT

The force exerted on a measuring section is broken down into two components each acting on one end of a measuring section. The components are each broken down into a vertical part and a horizontal part. The two vertical parts obtained are measured separately. The measured values are cyclically interrogated in an interrogation sequence in the direction of movement of the living being and stored, to permit the determination of force, location, duration and course in time. The measuring surface is subdivided lamellar-fashion at right angles to the direction of movement. One measuring section is narrower than the foot and longer than the track width. The force sensing device (3) comprises a rigid crossbeam which is borne on a sensing block (7) on both sides and acts in the vertical direction on a measured value delivering sensor (23) disposed therein. The crossbeam is mounted to move only vertically and borne on a measuring spring (43) which bears against the sensing block and is preferably a flat spring. The measured value delivering sensor measures the vertical movement of the measuring spring. A transmission element (47) is disposed between the measuring spring and the measured value delivering sensor and is acted upon in the direction of the measuring spring.

11 Claims, 7 Drawing Sheets

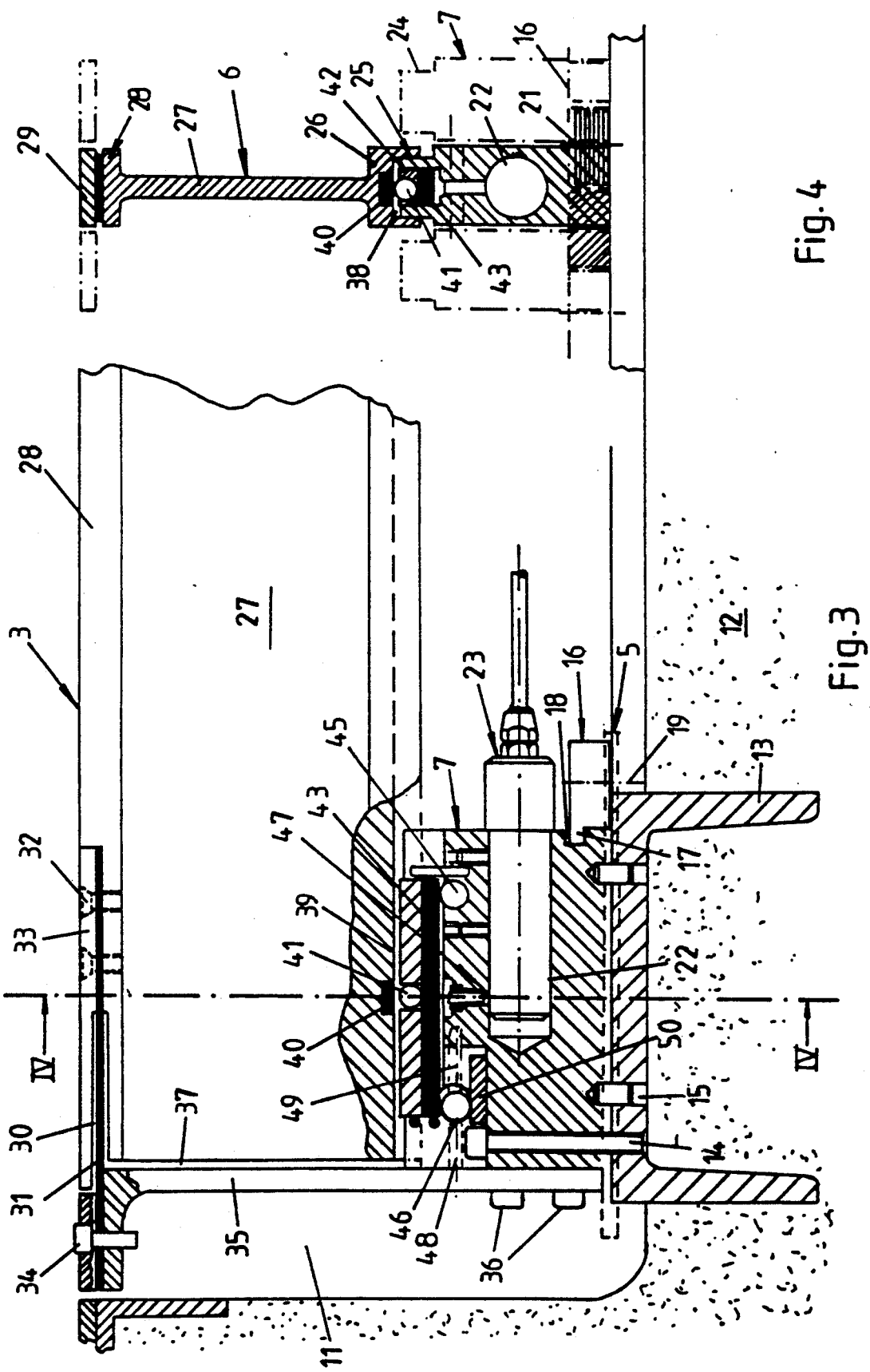

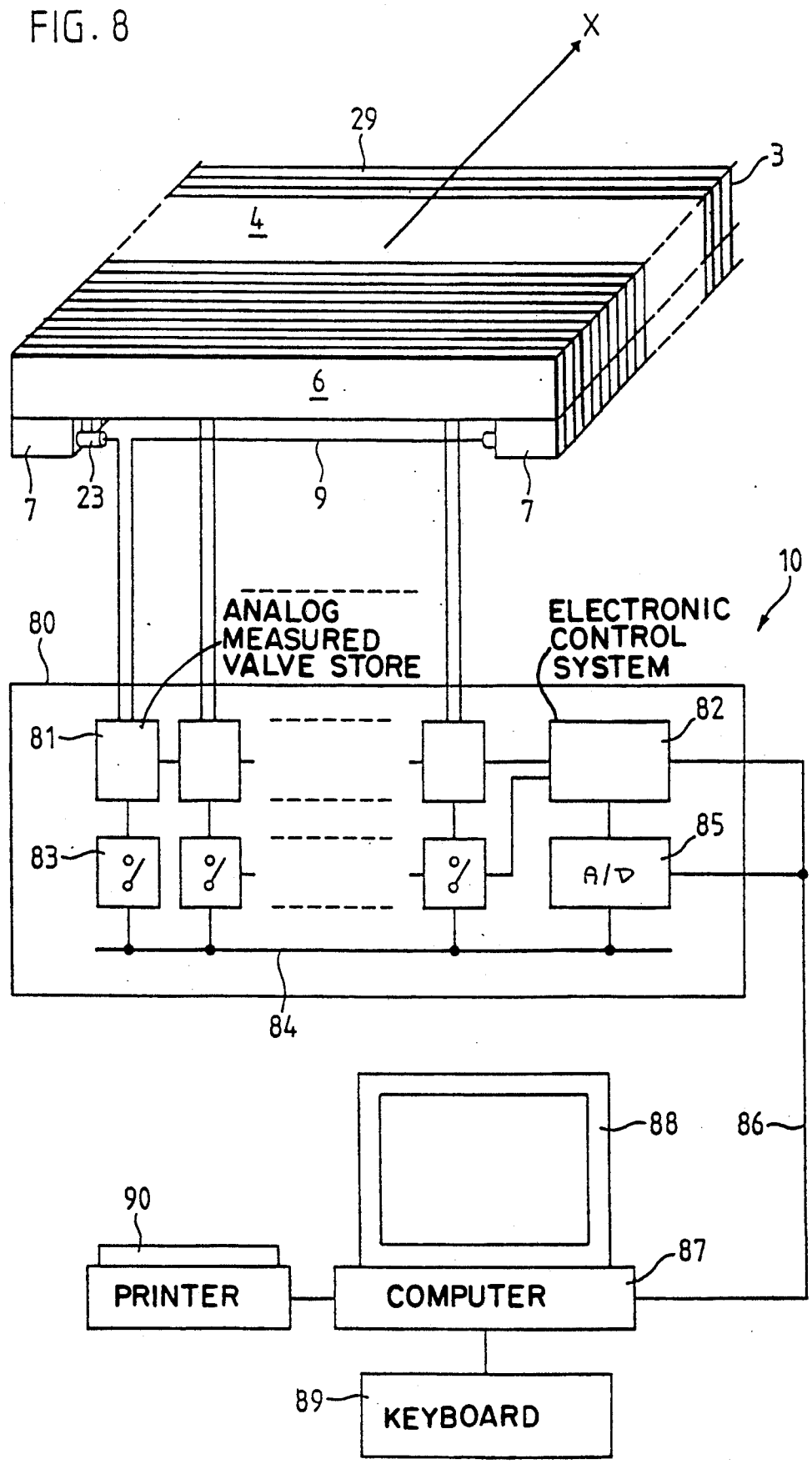

METHOD OF INVESTIGATING THE GAIT OF A LIVING BEING

BACKGROUND OF THE INVENTION

1. Field of the Invention

The invention relates to a method of investigating the gait of a living being, more particularly a horse, by measuring the force exerted by its feet on the ground and of the location, duration and course in time of the application of force in the zone of a substantially horizontal measuring surface taking the form of part of the ground, the measuring surface being subdivided substantially at right angles to the direction of movement of the living being into elongate measuring sections parallel to each other and adjacent in succession in lamellar fashion. The invention also relates to a corresponding apparatus, wherein a force sensing device having a substantially rectangular force sensing surface and a plurality of measured value delivering sensors connected to an electronic evaluating unit are associated with each measuring section.

The process and apparatus produces results which are mainly usable outside medicine as intermediate results for assessing the gait of the particular living being, even if they may be used when making a diagnosis, too.

More particularly in the case of highly valuable horses such as racehorses, it is found to be necessary to obtain the fact that such measured values give notice of abnormalities and can often throw light on their causes, such measured values provide information concerning the present condition (fitness) of the horse and its racing chances at the moment.

2. Discussion of the Prior Art

Since every horse has its own individual gait, the gait can be measured and stored with the animal perfectly healthy and giving its best performance. The gait is then available as a basic pattern for a subsequent comparison with fresh measurements. Regular gait analyses enable deviations from the basic pattern of the gait to be detected earlier on, more particularly before the horse shows lameness. As a result, for example, a horse in poor condition can be gently treated, or if necessary measures can be taken in good time to prevent the progress of a disease.

U.S. Pat. No. 4,233,845 states that the potential performance of a horse depends on the time during which two or more hoofs are simultaneously in contact with the ground during one step. The performance potential also depends on the time during which all four legs are simultaneously not in contact with the ground during one step. For these reasons U.S. Pat. No. 4,233,845 proposes that the horse should be put into a high speed gait and the time of contact determined during which contact with the ground is made and then discontinued during successive steps at this gait. The overlapping time during this step is also measured, and also the speed of the gait. Conclusions concerning performance potential are drawn from these results. To determine the contact with the ground and the corresponding contact times, use is made of a high speed camera or the sound of the steps is recorded on a tape recorder placed on the horse or on the ground, while the speed is measured based on running distance and clock measurements. These recording procedures are much too expensive, and moreover the results attainable are much too imprecise to enable the gait at the moment to be compared with a stored previous gait—i.e. to detect deviations from the basic pattern in good time.

U.S. Pat. No. 4,195,643 discloses a method of determining the relation between a limit of pain and the physiological compressive force to be ascribed to the pain. The physiological compressive forces are recorded by a pressure plate system to produce an analog output signal with a direct voltage and an alternating voltage component. In a suitable analyzer, the direct voltage component and the alternating voltage component are then separated, whereafter an output signal derived from the alternating voltage component is generated which quantifies the pain limit. However, the coming lameness of a horse cannot be diagnosed before a pain limit is reached, and this method is unsuitable for the early detection of deviations from the basic gait pattern.

WO-87/01574 and U.S. Pat. No. 4,267,728 disclose how to investigate the gait of a human being by measuring the force exerted on a measuring area by means of force sensing devices disposed parallel to each other and adjacent in succession and connected to an electronic evaluating unit. Not only the force exerted, but also the locations where the force is exerted and the position of such locations in relation to one another are also determined. The result is supposed to yield information concerning the geometry of the footprints as a function of time and the relative arrangement of the footprints and the strength of pressure. However, the duration corresponding to the successive steps and the corresponding sequence of the application of force in time are not determined with a resolution which would be suitable for the early detection of deviations from the basic gait pattern, since this is quite unnecessary in the intended use of these prior art systems, which are basically intended for investigating the biomechanics of the human gait with reference to diagnosis and therapeutic measures. Moreover, in the system disclosed in WO-87/01574 the person to be investigated walks on a soft mat, and in the system disclosed in U.S. Pat. No. 4,267,728 on transparent beams arranged successively in parallel, which arrangement cannot be used or extrapolated for a horse, since if a horse senses or sees a change in the structure of the ground it immediately alters its gait in reaction thereto.

The Paper by S. Hirokawa and K. Matsumara entitled "Gait analysis using a measuring walkway for temporal and distance factors" published in Medical & Biological Engineering & Computing 25 (September 1987), pages 577–582, discloses a system for investigating the human gait which is similar to the system disclosed in WO-87/01574 and has the same disadvantages, so that it also is unsuitable for the early detection of deviations from the basic gait pattern, more particularly of a horse.

It is also known from U.S. Pat. No. 4,195,643 to investigate the gait of a living being (human being or horse) also by measuring the force exerted on a measuring surface by means of force sensing devices disposed parallel to each other and adjacent in succession and connected to an electronic evaluating unit. This system also determines not only the force exerted, but the locations of the exertion of force and the position of the locations in relation to one another. The result is supposed to yield information concerning the relative arrangement of the footprints of the human being or horse, and also the strength of the pressure as a function of time. However, in this system also the duration corresponding to the successive steps and the corresponding cause of the application of force in time is not determined with a resolution which would be suitable for the early detection of deviations from the basic gait pattern, since this is quite unnecessary in the intended use of the system, which is mainly aimed at investigating the biomechanics of the gait with reference to diagnosis and therapeutic measures. Moreover, the structure and dimensions of the measuring area provided cannot be used or extrapolated for investigating the gait of a horse; on the one hand the measuring area extends above the ground, which arrangement cannot be used for a horse, since the horse would immediately alter its gait in reaction thereto, and on the other hand the measuring surface with its dimensions of about 60×60 cm (whether subdivided or not) is unsuitably dimensioned and proportioned for the early recognition of deviations from the basic pattern of the sporting gait (running in human beings, trotting or galloping in horses), since this requires a substantially wider and longer measuring area.

CH-658726 and CH-669256 propose hydraulic pressure sensing devices for the measurement of the force exerted on a measuring surface by means of force sensing devices disposed parallel to each other and adjacent in succession and connected to an electronic evaluating unit. An incompressible liquid is disposed in a resilient tubular casing which can be acted upon by an external pressure, the casing being connected to a manometer or transducer. The wall of the tubular casing which receives the pressure is connected via the liquid to a pressure-transmitting longitudinal reinforcement. These devices merely determine the strength of a pressure. It is true that this may throw some light on the gait of a horse, but it is not adequate for the assessment of the gait.

U.S. Pat. No. 3,906,931 suggests electromechanical pressure sensing devices for the measurement of the force exerted on the measured area and of the locations where the force is exerted and the position of the locations in relation to one another. A number of strain gauges are disposed in four resilient rings acted upon by an external pressure. This apparatus actually allows instantaneously or as a function of time the determination of not only the total force exerted, but also of the locations where the force is exerted and the position of the locations in relation to one another, but the apparatus is intended solely to investigate the stance of a human being: it is unsuitable for investigating the gait of a human being, let alone for investigating the gait of a horse.

Apparatuses of a similar kind and having the same disadvantages are also known, for example, from U.S. Pat. No. 3,340,726 and U.S. Pat. No. 3,090,226.

Magnetic path sensors which can be used for the measurement of force are mentioned in general and briefly described in the "Manual of the electric measurement of mechanical values" by C. Rohrbach, published by VDI (Düsseldorf, 1967).

SUMMARY OF THE INVENTION

In view of the prior art, it is an object of the invention to provide a method and apparatus by means of which the gait of a living being, more particularly a horse, can be exhaustively investigated, so that early detection of deviations from the basic gait pattern, more particularly the sporting gait (respectively: walking or running, trotting or galloping) is made possible.

To solve this problem it is first necessary to determine not only the force exerted, but also the locations of the exertion of force and the position of such locations in relation to one another, and also the duration and course in time of the application of force. This means that three parameters are adduced for an exhaustive assessment of gait. On the one hand, the force exerted on the force sensing device is measured directly. Parallel herewith, in a suitable control and evaluating unit a time scale is recorded which indicates, for example, for how long a foot applies a particular force. For example, a horse will load a weak or diseased leg more briefly with a certain force than a normal or healthy leg. However, it is also of primary importance to determine those locations at which the living being applies its feet, and to bring such locations into relation with one another. For example, a horse with a lame front leg will take a shorter step than one with a healthy leg. Thus, if these three parameters, force, time and location are brought into relation with one another and processed by a suitable evaluating unit, any abnormality in the gait and any deviation from a basic or earlier gait pattern can be detected.

Furthermore, for the solution of the problem the measuring area must have a texture which is very similar to the normal ground in mechanical, acoustic and optical respects, since the living being should notice no difference between the normal ground and the measuring area. More particularly, the measuring area must have no noticeably springy elements or parts and it must look and sound like the surrounding normal ground.

The force sensing devices must therefore enable an adequate resolution to be achieved in the direction of movement of the living being to ensure both an adequately accurate local determination of the loads occurring and also corresponding distance measurements between the different extremities of the living being. On the other hand, however, for practical reasons of the limited space available, the scanning time needed for the interrogation of the total measuring area, etc., and last but not least for reasons of cost, it is impossible to increase the number of force sensing devices to just any extent.

Consequently, the individual force sensing devices must be narrow, but nevertheless rigid and resistant, and their force sensing area must be of a given texture, adapted to the living being to be investigated. Forces up to 5000 Newton must be capable of being measured. This in its turn results in the requirement of a compact but solid structure of the actual measured value delivering sensors for force measurement and of a measuring path of the measuring value delivering sensors which must be unnoticeably small.

To solve the problems stated, while maintaining the given conditions, the method according to the invention is characterized in that a force exerted by the living being on a measuring section is broken down into two components, one of each acts on the measuring section adjacent a respective end thereof; the two components are each broken down into a vertical and a horizontal part; and the two vertical parts thus obtained are then measured separately to give in each case a measured value which is cyclically interrogated in the course of an interrogation sequence corresponding to the succession of measuring sections in the direction of movement of the living being and stored, to be subsequently interpreted in the investigation of the gait of the living being.

In a preferred embodiment of the method according to the invention, the measured values are on the one hand put into intermediate storage and on the other hand compared with a predetermined threshold value, and only those measured values put into intermediate storage which exceed the threshold values are passed on for an evaluation wherein the sum of the two measured values is formed for the determination of the total force exerted vertically on the measuring section and the ratio between the difference in the two measured values and their sum is formed to determine the location where the force is exerted on such measuring section.

In a preferred variant embodiment of the method according to the invention, to determine the total force exerted vertically on a measuring section, the sum of the two measured values is formed, such sum is on the one hand put into intermediate storage and on the other hand compared with a predetermined threshold value, and only those values of the sum put into intermediate storage which exceed the threshold value are passed on for evaluation.

Furthermore, according to the invention it is preferred that those values put into intermediate storage which exceed the threshold value are subjected to an analog-to-digital conversion, if necessary after an amplification, while a digital identification of the or each corresponding measured value delivering sensor and a digital statement of time are associated therewith, and each value which is being passed on for evaluation is stored together with its identification and its statement of time.

Also, according to the invention it is preferred that the cyclic interrogation sequence is initiated only on the occurrence of a value put into intermediate storage which exceeds the threshold value, and the interrogation sequence is automatically discontinued if during a predetermined period no occurrence has been detected of a value put into intermediate storage which exceeds the threshold value.

To solve the problem stated, while maintaining the conditions stated, the apparatus according to the invention is characterized in that the width of the individual measuring section is smaller than the length of the foot of the living being and the length of the measuring section is greater than the track width of the living being, and the force sensing device comprises a stiff crossbeam on whose upper surface the measuring section is disposed and which is borne on both sides adjacent each of its ends on a sensing block and acts therein in the vertical direction on a measured value delivering sensor.

Preferably the apparatus according to the invention is so constructed that the crossbeam in the force sensing device is mounted to move substantially only vertically and is borne on a measuring spring which bears against the sensing block; the measured value delivering sensor is a path sensor for the vertical movement of the measuring spring; and a transmission element for the vertical movement of the measuring spring is disposed between the latter and the measured value delivering sensor, the transmission element being operatively connected to the measured value delivering sensor and acted upon by resilient means in the direction of the measuring spring.

Also preferably the apparatus according to the invention is so constructed that the measuring spring takes the form of a flat spring and is so disposed in the sensing block that its bending is limited by its coming into contact with a stationary part of the sensing block; and the substantially vertically extending transmission element has a rod section and a tappet rod adjoining the bottom end of such rod section and a sliding member adjoining the top end of such rod section, the sliding member being guided in the vertical direction in a guide sleeve provided in the sensing block and having in its upper portion a head which is engaged from below by a sealing disc bearing against the sensing block and comprises an adjusting device whose top end has a receiving depression for the bottom part of a ball whose top part bears against the measuring spring.

Preferably also the apparatus according to the invention is so constructed that there is disposed between the cross-beam and the measuring spring a ball or roller which is trapped in a matching ball receptacle in the sensing block and is borne on the measuring spring substantially in its center, the measuring spring being mounted on two rollers which are spaced from one another and symmetrically from the center of the measuring spring and are disposed substantially parallel with one another and at right angles to the longitudinal direction of the measuring section, one roller being stationary in relation to the sensing block and the other roller being movable.

In addition, preferably the apparatus according to the invention is so constructed that the sensing block contains a rail strip in which the measuring spring and the ball are received and which is engaged from above in roof fashion by a U-shaped sectional strip provided on the crossbeam.

The apparatus according to the invention is also preferably so constructed that the crossbeam is mounted in the force sensing device on at least one beam extending upwardly from the sensing block and is connected to such beam via a substantially horizontal spring strap, and the force sensing devices are inserted in a groove, the sensing blocks each being attached in two parallel rows to a foundation section, let into the bottom of the groove, by means of threaded bolts and clamping blocks connected to the foundation section, such clamping blocks having lugs engaging in grooves in the sensing blocks and being so disposed offset in relation to the sensing blocks that fastening screws associated with the clamping blocks are accessible to a screwdriver inserted from above between the measured value delivering sensors inserted in the sensing blocks.

Furthermore, the apparatus according to the invention is so constructed that a number of force sensing devices are disposed together on an auxiliary assembly frame, the clamping blocks being connected via the attaching screws to the auxiliary assembly frame, and the latter and the individual sensing blocks being connected via the threaded bolts to the foundation section.

Preferably the apparatus according to the invention is also so constructed that the measured value delivering sensor comprises permanent magnets, magnetically sensitive sensor elements and attaching elements, the attaching elements being made of a resilient material and movably retaining the sensor elements and having a resilient pre-stressing which acts on the sensor elements in the direction of the tappet rod.

The invention achieves, among others, the following advantages.

Independently of the length of the measuring section (i.e. of the crossbeam) and of the location at which the force is exerted thereon, the resulting vertically exerted force is always accurately measured. The number of measuring locations is reduced by arranging a sensing block on both sides of the transverse beam adjacent each end thereof, which arrangement shortens the interrogation cycle and therefore makes a high measuring speed possible.

However, the location of the application of force can be determined without interrogating additional measured value delivering sensors and therefore without slowing down the measuring method. There are stored only the measured values of those force sensing devices which experience a load, together with an identification and a statement of time, which procedure reduces the amount of storage required; clearly, the corresponding threshold value can be controlled and if necessary changed by software. Storage capacity is also saved by the feature that the cyclic interrogation sequence begins only when usable measured values are present, and is discontinued spontaneously when it is highly probable that no further usable measuring results are to be expected. The clock rate of the interrogation cycle can also be controlled by software, which feature enables the measuring speed and storage capacity available to be adapted to different speeds of movement of the living being.

Between successive interrogations of a measured value delivering sensor, its zero point (i.e. the measured value transmitted by the measured value delivering sensor when the force sensing device experiences no load) can be determined and compensated. This is particularly advantageous, since shifts of the zero point can occur, for example, due to changes in temperature and would have a particularly interfering effect precisely on the very high precision measurements required, if it were impossible to compensate the zero point.

The measuring spring can readily be exchanged for a suitably thicker or thinner measuring spring, which possibility substantially simplifies adaptation to different measuring conditions. It is moreover impossible for the measuring spring to be overloaded, since at its maximum sag it is abutting on the sensing block and cannot sag further (i.e. excessively).

The sag of the measuring spring is measured substantially free from wear by means of a measured value delivering sensor operating on a magnetic principle, which results in an excellent linearity of the conversion from path to electrical signal in the measured value delivering sensor. The kinematic transmission chain from the crossbeam via the measuring spring to the sensor element, together with the pre-stressing of the sensor element in the direction of the tappet rod, ensures that the vertical movement of the crossbeam takes place without play or hysteresis on the sensor element, which arrangement enables highly sensitive sensor elements to be used and the vertical movement of the crossbeam kept so small that it is not noticed by the living being. This also enables the measuring surface and surrounding ground to be given a common covering, so that the living being does not notice the measuring surface at all.

The rail strip which is provided in the sensing block and receives the measuring spring and the ball and is engaged over roof-fashion by a U-shaped sectional strip provided on the crossbeam ensures that precipitation entering the apparatus from above do not reach the measuring zone or the kinematic transmission chain from the crossbeam via the measuring spring to the sensor element.

The assembly of the apparatus is facilitated by the feature that the attachment of the force sensing devices can be accessed and operated on from above between the measured value delivering sensors, and an auxiliary assembly frame can be used. The bearing of the crossbeams on beams which extend upwardly from the sensing blocks and to which the crossbeams are connected via substantially horizontal spring straps enables any horizontal displacement of the crossbeams to be avoided, so that only the vertical movement is transmitted.

The measured values transmitted by the force sensing device can be of both a dynamic and a static nature. The dynamic measurement is performed in a manner true to reality by a low-delay measuring system with high cycle rates. The measurement of purely static loading, in which the interrogation cycle must be triggered manually, enables the apparatus according to the invention to be used as a balance. As a whole, the result is an apparatus which performs a comprehensive and reliable investigation of the gait of a living being, more particularly a horse, so that abnormalities in the gait can be detected at a very early stage.

BRIEF DESCRIPTION OF THE DRAWINGS

Further advantages, features and details of the invention can be gathered from the following description of preferred embodiments of the method and the apparatus, with reference to the drawings, wherein:

FIG. 3 is a longitudinal section through an end portion of a force sensing device according to the invention, FIG. 4 is a cross-section through a force sensing device according to the invention, taken along the line IV—IV in FIG. 3, FIG. 8 is a basic diagram of the processing of measured values in the apparatus according to the invention.

DESCRIPTION OF THE PREFERRED EMBODIMENTS

Figure 1:
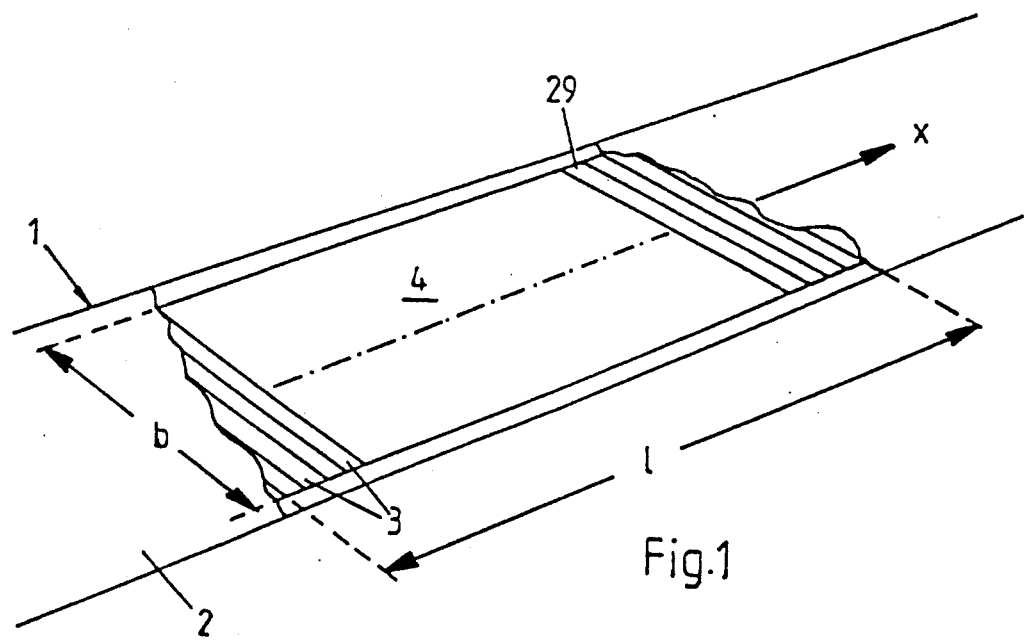
FIG. 1 shows a partially opened-up guide track for the investigation of the gait of a living being, for example, a horse.

FIG. 1 shows a guide track 1 along which, for example, houses are guided, and which has a cover 2. The cover 2 is, for example, a carpet of plastics, rubber or the like and serves to protect force sensing devices 3 and to create as homogeneous a running surface as possible, so that, for example, a horse guided over the guide track 1 is not influenced by differences in the surface.

The actual measuring surface 4 has, for example, a length 1 of about 4000 mm and a width b of about 800 mm and is disposed under the cover 2. The measuring surface 4 is substantially horizontal and forms part of the ground, being subdivided substantially at right angle to the direction of movement X of the living being into measuring sections 29. The measuring sections 29, of which only a few are shown in FIG. 1 to make the drawing clearer, are elongate in construction and disposed parallel to each other in lamellar fashion, and to each measuring section corresponds a force sensing device 3 having a substantially rectangular force sensing surface. The width of the individual measuring section 29 is, for example, 25 mm and is therefore smaller than the length of the horse's foot, while the length of the measuring section 29 is equal to the width b of about 800 mm of the measuring surface 4 and is therefore larger than the horse's track width.

Figure 2:
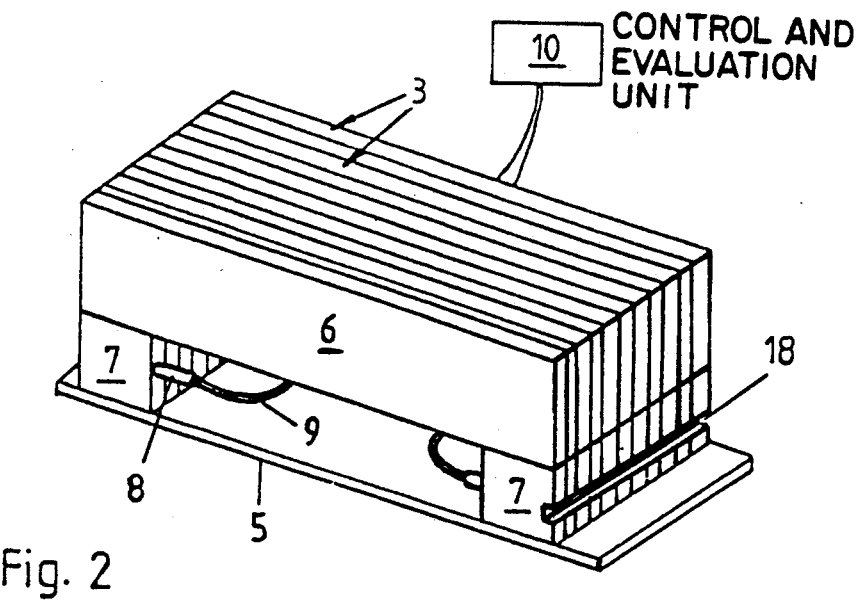
FIG. 2 shows a perspective view of a series of force sensing devices according to the invention mounted on an auxiliary assembly frame.

As shown in FIG. 2, a plurality of force sensing devices 3 are disposed on an auxiliary assembly frame 5. Each individual force sensing device 3 comprises a rigid crossbeam 6 which is borne in relation to the assembly frame 5 on both sides on a sensing block 7 at each of its ends and on whose upper surface the measuring portion 29 is disposed. Each sensing block 7 has a plug-in connection 8 for a measured value delivering sensor 23 (FIG. 3) inserted in the sensing block 7. A connecting cable 9 extends from the plug-in connection 8 to a corresponding electronic control system and evaluating device 10, which will be explained in greater detail with reference to FIGS. 8 to 10.

FIG. 3 shows a detail of a force sensing device 3 which is inserted in a corresponding groove 11 below the guide track 1. The detail shown is one end part of the apparatus illustrated, the other end part being substantially symmetrical in relation thereto. The force sensing devices 3 are anchored or attached to a base 12 via a foundation section 13.

The sensing blocks 7 are each attached in two parallel rows to the foundation section 13 let into the bottom of the groove by means of threaded bolts 14 and clamping blocks 16 connected to the foundation section 13. To secure the sensing blocks 7, the clamping blocks 16 have lugs 17 engaging in grooves 18 in the sensing block 7. The clamping blocks 16, as can be seen in FIG. 4, are so disposed offset in relation to the sensing blocks 7 that attaching screws 19 associated with the clamping blocks 16 are accessible from above between the measured value delivering sensors 23 inserted in the sensing blocks 7, since each time a bore 21 for the attaching screw 19 is provided between two blind bores 22 and between two measured value delivering sensors 23 in the assembled condition of the apparatus.

Each sensing block 7 either can be connected directly via a threaded bolt 14, while being centered by guide bolts 15, to the foundation section 13 or the auxiliary assembly frame 5, or the auxiliary assembly frame 5 shown in chain lines can be interposed therebetween and carry an assembly of a number of force sensing devices 3. A number of such auxiliary assembly frames 5 can also be used disposed in succession. Each clamping block 16 can then be connected via the attaching screw 19 to the auxiliary assembly frame 5, and the auxiliary assembly frame 5 and the individual sensing blocks 7 can be connected via the threaded bolts 14 to the foundation section 13.

The sensing block 7 forms via a shoulder-like step 24 a rail strip 25 which is engaged around and over roof-fashion by a U-shaped sectional strip 26 of the crossbeam 6. This prevents, for example, precipitation and rain water from penetrating into the actual measuring zone of the force sensing device 3.

Besides, the crossbeam 6 is a rigid aluminum section, the U-shaped sectional strip 26 being adjoined by a wall strip 27 which widens upwards in T-shape. The T-shaped strip 28 forms in the outward direction a top surface of the measuring section 29 which lies below the cover 2. On the edge side the T-shaped strip 28 is formed with a substantially horizontal slot 30 into which a substantially horizontal spring strap 31 is inserted. The spring strap 31 and the T-shaped strip 28 are connected via countersunk screws 32. The insertion of the spring strap 31 is moreover simplified by this part of the T-shaped strip 28 being constructed as a cover strip 33 which is applied only when the spring strap 31 is screwed with the countersunk screws 32.

On the other hand the spring strap 31 is connected via a screw 34 to a beam 35 which is fixed by other screws 36 on the sensing block 7 and extends upwardly therefrom. As a result the crossbeam 6 is mounted on the beams 35 in the force sensing device 3. The spring strap 31 prevents any sideways tilting of the crossbeam 6, thereby enabling the vertical force components to come into play, i.e. the crossbeam 6 is mounted substantially only with provision for vertical movement in the force sensing device 3. A gap 37 is also left between the beam 35 and the crossbeam 6 to allow for changes in the length of the crossbeams 6 caused by any changes in temperature. The U-shaped sectional strip 26 also forms a groove 38, a piece of hard metal 40 being let into the bottom 39 of the groove at a predetermined location. When the apparatus is assembled, the piece of hard metal 40 bears against a ball 41 disposed in a ball receptacle 42 in the rail strip 25; a roller can be used instead of a ball 41. The ball or roller 41 bears against a measuring spring 43 which takes the form of a flat spring and is also received in the rail strip 25. The measuring strip 43 is borne on both sides on cylindrical, hardened rollers 45, 46 and in this way bears against the sensing block 7 via two rollers 45, 46 which are spaced from one another and symmetrically from the center of the measuring spring 43 and are disposed substantially parallel with one another and at right angles to the longitudinal direction of the measuring section 29. The force exerted on the crossbeam 6 and on the top surface of the measuring section 29 via the ball or roller 41 substantially on the center of the measuring spring 43. The corresponding vertical movement of the measuring spring 43, i.e. the sag of the measuring spring 43 proportional to the force operating, is sensed by a transmission element 47 which is disposed between the measuring spring 43 and the measured value delivering sensor 23 and is operatively connected to the measured value delivering sensor 23. The measured value delivering sensor 23 is constructed as a path sensor and delivers an electric signal which corresponds to the vertical movement of the measuring spring 43. Adaptation to a required force-measuring range is possible by suitable dimensioning of the interchangeable measuring spring 43. The measuring spring 43 is also so disposed in the sensing block 7 that its sag is limited by its abutment on a fixed part of the sensing block 7, so that the measuring spring cannot be overloaded by excessive sag.

While the roller 45 is fixed into the sensing block 7, the other roller 46 is movably mounted and bears on the one hand against a pin 43 shown in chain lines and on the other hand against a helical spring 49. In this way the roller can roll by a predetermined amount over a corresponding plate 50 in accordance with the sag of the measuring spring 43. This provision of a one-sided movable bearing of the measuring spring 43 against the roller 46 eliminates hysteresis and enhances measuring accuracy.

Figure 7:
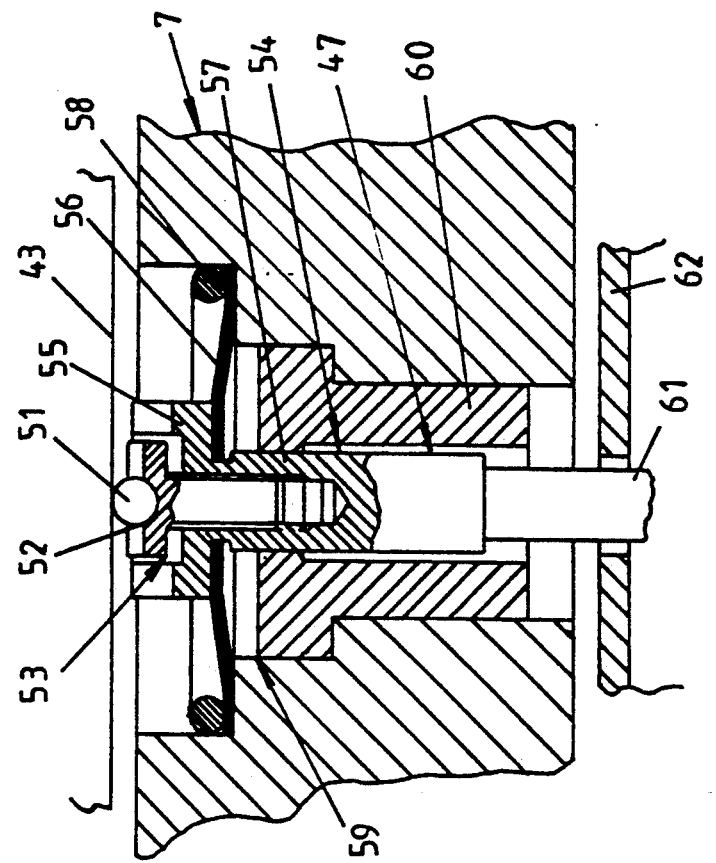
FIG. 7 shows part of FIG. 3 to an enlarged scale.
Figure 6:
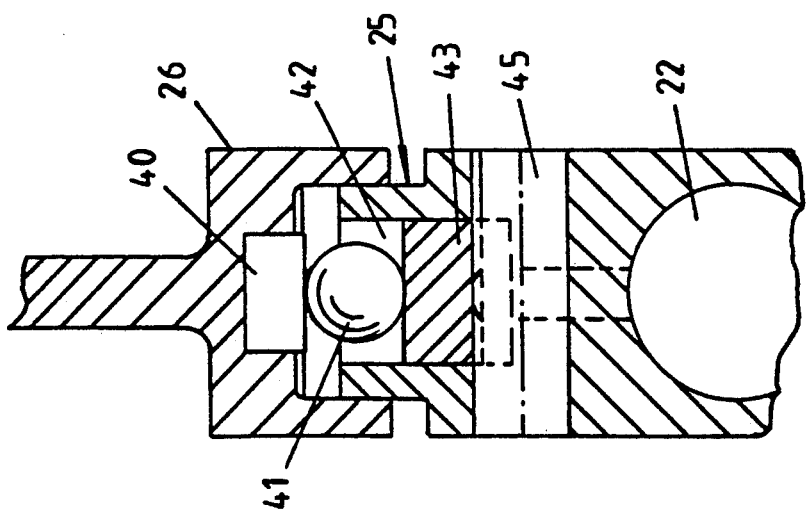
FIG. 6 shows part of FIG. 4 to an enlarged scale.

As shown in FIG. 7, the measuring spring 43 acts on another ball 51 which is already part of the transmission element 47. The ball 51 rests in a matching receiving depression 52 in an adjusting device 53 inserted in a sliding member 54. The sliding member 54 has a head 55 which is, for example, a round head and bears against a sealing disc 56 when the apparatus is assembled. The sealing disc 56 encloses a portion 57 of the shank of the sliding member 54 and is fixed by a clamping ring 58 in a part of a stepped bore 59 with which the sensing block 7 is formed. The sliding member 54 also extends through the stepped bore 59, the portion 57 of its shaft being guided by a guide sleeve 60.

After the portion 57 of the shank, the transmission element 47 merges into a rod portion 61 which engages the measured value delivering sensor 23 through a wall 62 thereof. This rod portion 61 is then followed in the measured value delivering sensor 23 shown in FIG. 5 by a tappet rod 63 which is disposed in a hood 64 and bears there against a ball 65. Should it be found necessary, the hood 64 can also bear against the bottom wall 62 or a steel ring 66. In this way the hood 64 can then follow the movement of the tappet rod 63.

Figure 5:
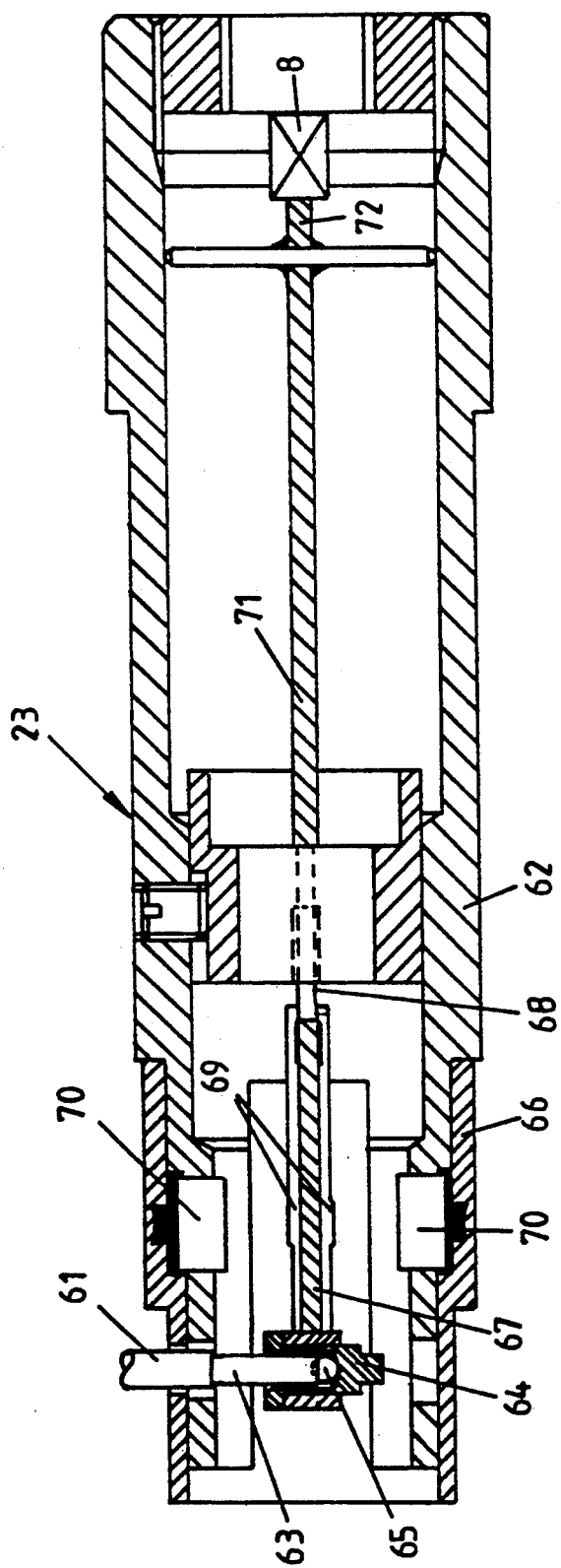
FIG. 5 is a longitudinal section to an enlarged scale through a measured value delivering sensor according to the invention.

In the embodiment shown by way of example in FIG. 5, the measured value delivering sensor 23 comprises permanent magnets 70, magnetically sensitive sensor elements 69 which are constructed, for example, as Hall effect sensors or magnetoresistive sensors, and also attaching elements 68, while a steel ring 66 ensures the magnetic connection. The attaching elements 68 are made of a resilient material being, for example, wire springs, and are used for the movable retention of the sensor elements 69. The attaching elements 68 have a resilient pre-stressing which acts on the sensor elements 69 in the direction of the tappet rod 63.

The hood 64 is connected via a strip 67 to the attaching elements 68, which are so pre-stressed and designed that even without the aforementioned additional helical spring, they allow the positioning and return of the sensor elements 69, which they act upon in the direction of the measuring spring 43.

The substantially vertically extending transmission element 47 therefore has a rod portion 61, a tappet rod 63 adjoining the bottom end of the rod portion 61, and a sliding member 54 adjoining the top end of the rod portion 61. The sliding member 54 is guided in the vertical direction in a guide sleeve 60 provided in the sensing block 7 and has a head 55 in its upper portion. The head 55 is engaged around by a sealing disc 56 bearing against the sensing block 7 and comprises an adjusting device 53 whose top end has a receiving depression 52 for the bottom part of a ball 51 whose upper part bears against the measuring spring 43. This arrangement enables the sag of the measuring spring 43 to be scanned without wear; the result is high measuring sensitivity accompanied by an excellent linearity relationship between the vertical path of the crossbeam 6 and the electric signal delivered by the measured value delivering sensor 23 near to the attaching elements 68.

Via flexible braided connections, which are not shown in FIG. 5 and extend substantially adjacent the attaching elements 68 and bearing elements 71, 72 in parallel therewith, the sensor elements 69 are connected first to the plug-in connection 8 and via the latter to an electronic circuit or evaluating unit which will be disclosed in greater detail hereinafter. The two sensor elements 69 of each individual measured value delivering sensor 23 deliver signals of opposite direction or polarity which are combined with one another in known manner in the electronic evaluating unit, to eliminate any direct voltage components and induced unwanted signals (mains frequency hum and the like) by means of socalled suppression of the common mode. Also in known manner the sensor elements 69 can be supplied with direct or alternating current, and there can also be an impedance transformation of the signals of the sensor elements 69 in relation to the input impedance of the circuit intended for the subsequent processing.

These known steps are familiar to an electronics engineer and will not be described in detail.

If required, the aforementioned electronic circuit or evaluating unit can be disposed at least partially on the supporting elements 71, 72. The supporting elements 71, 72 can also be constructed as a part of the printed circuit board bearing the electronic circuit: a certain portion of the length of the aforementioned flexible braided connections can also be borne on the printed circuit boards or if necessary applied as a printed line.

FIG. 8 is a basic diagram of the processing of measured values in the apparatus according to the invention. In an electronic measuring system 80 the signals of the individual measured value delivering sensors 23 are each supplied via lines 9 to an analog measured value store 81 and stored therein in analog manner in dependence of control by an electronic control system 82. Also in dependence of control by the electronic control system 82, the signals stored in the measured value stores 81 are passed on in succession via switches 83 to a common line 84 and then an analog-to-digital converter 85. The digital signals appearing on the output line 86 of the analog-to-digital converter 85 are processed and displayed in a computer 87 acting as an evaluating device and having a monitor 88, a keyboard 89 and if necessary a printer 90.

Figure 9:
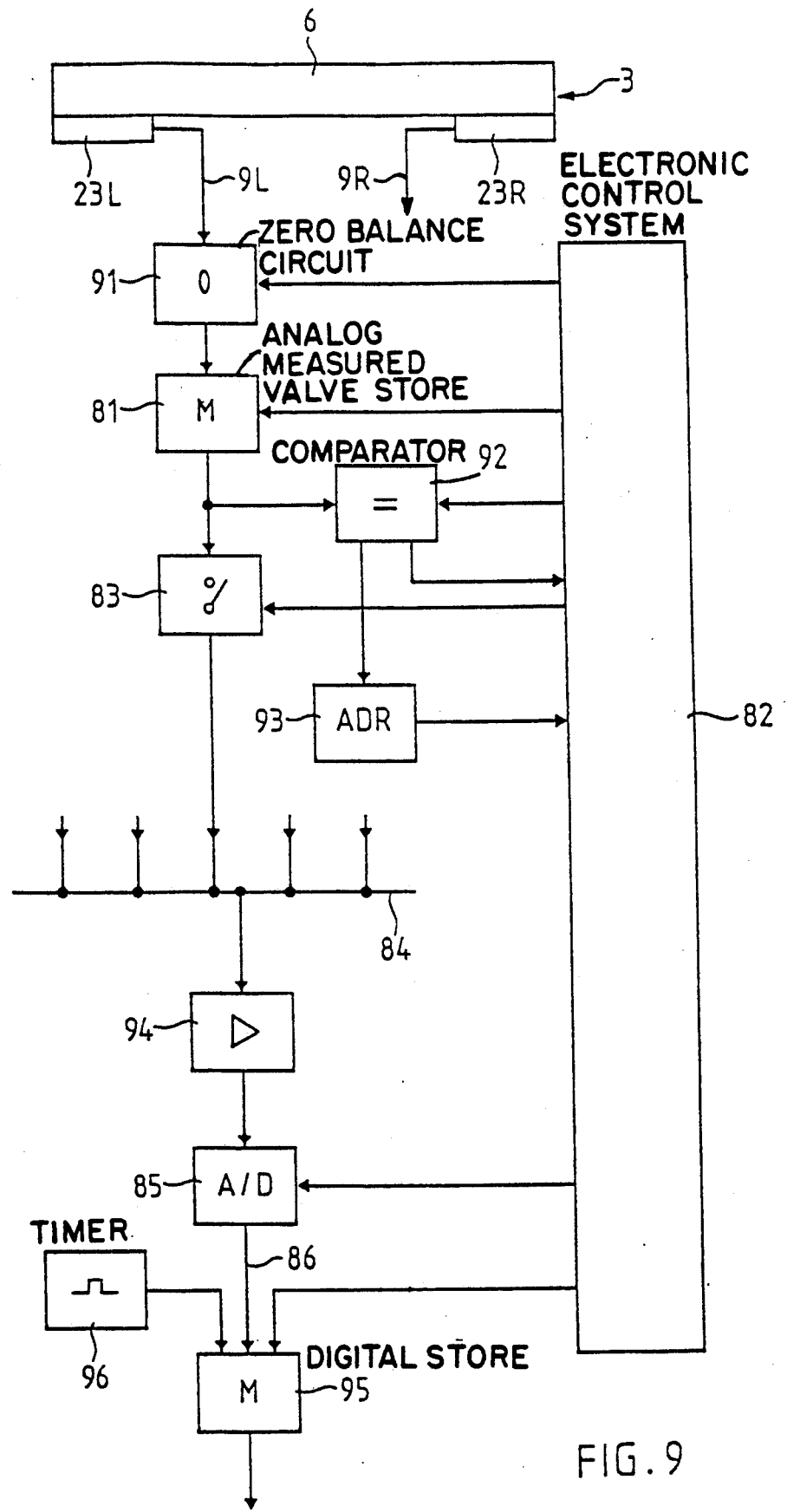
FIG. 9 is a block diagram of an embodiment of the processing of measured values in the apparatus according to the invention.

FIG. 9 is a block diagram of an embodiment of the processing of measured values. This embodiment relates to the separate processing of the measured values of all the measured value delivering sensors.

To make the drawing clearer, FIG. 9 shows only two measured value delivering sensors, each of which is associated with one end of a particular crossbeam 6 and which are denoted by the references 23R and 23L, their connecting cables being denoted by 9R and 9L, the R in the references standing for "right" and L for "left". Again to make the drawing clearer, in the description of this embodiment only the processing of measured values in connection with the measured value delivering sensor 23L and the connecting cable 9L will be explained, since the explanation would be identical for the other measured value delivering sensors 23.

A zero balance circuit 91 (block "0") for determining and compensating the zero point of the measured value delivering sensor 23L (i.e. the measured value delivered by the measured value delivering sensor 23L when the force sensing device 3 experiences no load) is connected in series between the measured value delivering sensor 23L and the associated measured value store 81 (block "M"). The signal which initiates the zero balance procedure in the circuit 91 is delivered by the electronic control system 82. When the zero balance has been performed, it is retained up to the interrogation of the measured value of the measured value delivering sensor 23L and the transmission of its measured value by the measured value store 81, for example, for 2 minutes if no interrogation has taken place earlier. Then the zero balance procedure is repeated, although it may also be repeated at longer intervals of time.

The measured value store 81 acts as an intermediate store up to the interrogation of the measured value of the measured value delivering sensor 23L. In addition, the measured value put into intermediate storage is compared in a comparator 92 (block "=") with a threshold value which is delivered by the electronic control system 82 and can if necessary be adjusted in the software. If the threshold value is exceeded, the interrogation of the measured value put into intermediate storage in the measured value store 81 is released for access, although such interrogation takes place only when it is the turn of the particular force sensing device 3 in the cycle. The interrogation of the measured values exceeding the threshold value takes place by the successive switching on of the corresponding switches 83, and always in the running direction X (FIGS. 1 and 8), i.e. from the first to the last of, for example, 160 force sensing devices 3, and back to the first one, in periodic repetition.

For all the other measured value delivering sensors 23L and their associated circuit up to and including their associated switches 83, similar connections to the common line 84 are provided, as shown on the common line 84 in FIG. 9.

When the switch 83 is switched on, the analog measured value put into intermediate storage in the measured value store 81 passes to the common line 84 and thence via an analog amplifier 94 to the analog-to-digital converter 85, which is also subordinated to the electronic control system 82. The measured value then converted from analog to digital is passed on to a digital store, where it is inputted.

Simultaneously with the switching on of the switch 83, an identification or address delivering sensor 93 (block "ADR") is interrogated by the electronic control system 82, the identification of the interrogated measured value delivering sensor 23L thus delivered is read by the electronic control system 82 and passed on to a digital store 95 and inputted there. Also simultaneously with the switching-on of the switch 83, a statement of time from a timer 96 is inputted into the digital store 95. This timer 96 also determines the cycle and measuring speeds and can be adjusted in the software. For each measurement, therefore, the identification of the interrogated measured value delivering sensor 23, the corresponding measured value and the corresponding statement of time are stored together digitally in the digital store 95. This enables the evaluating device (computer 87 in FIG. 8) to precisely determine the location, time and force for each measurement.

When the measurement has been performed, the electronic control system 82 opens the switch 83 and therefore interrupts transmission, the analog measured value store 81 is reset, and the next force sensing device 3 following in the cycle and whose measured value exceeds the threshold value is then interrogated.

Figure 10:
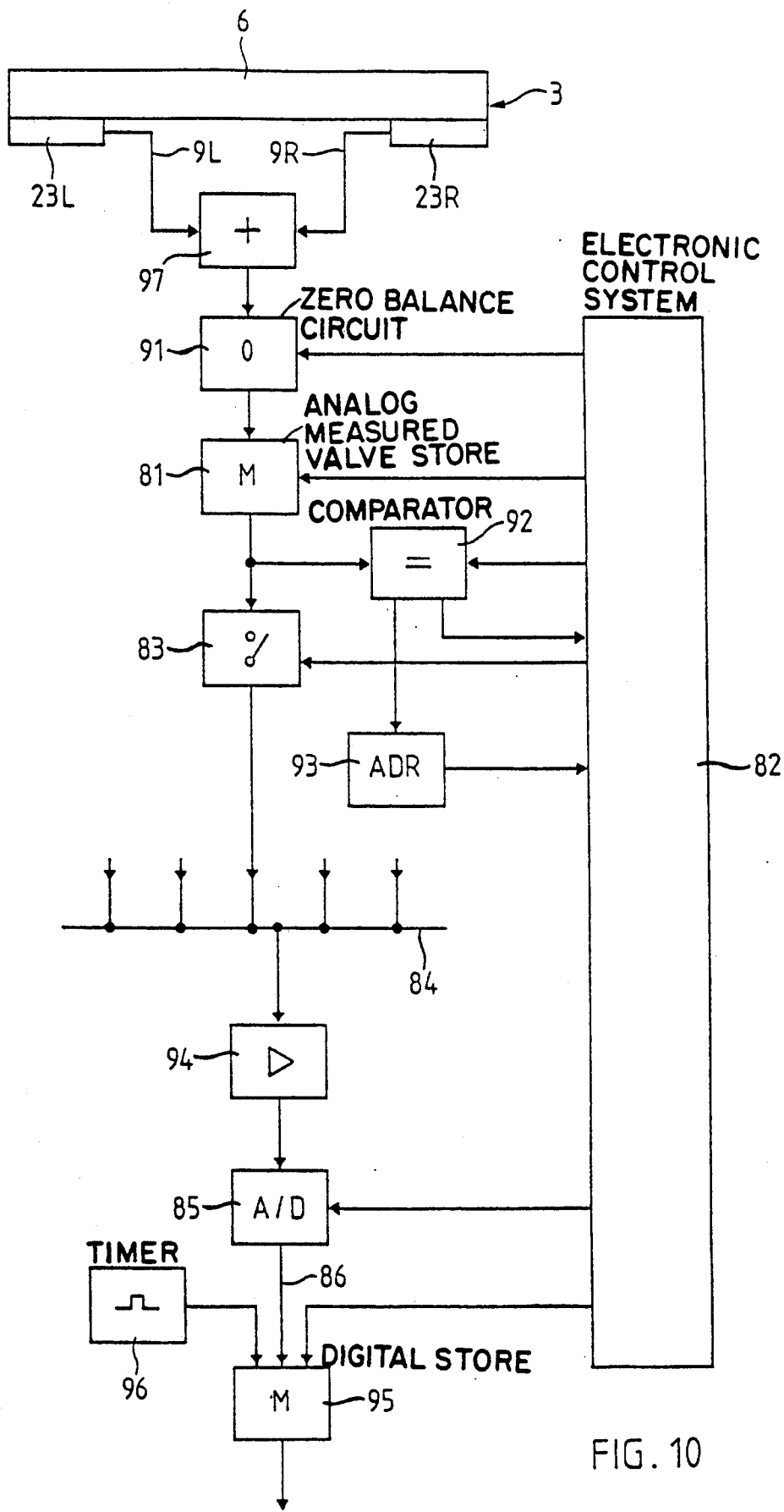
FIG. 10 is a block diagram of another embodiment of the processing of measured values in the apparatus according to the invention.

FIG. 10 is a block diagram showing another embodiment of the processing of measured values. This embodiment relates to the particular processing of the sum of the measured values of both the measured value delivering sensors 23R and 23L of a particular crossbeam 6 and to the processing of that sum for all crossbeams 6 in succession.

Again to make the drawing clearer, FIG. 10 shows only two measured value delivering sensors each of which is associated with one end of a particular crossbeam 6 and is denoted by the references 23R and 23L, their connecting cables being denoted by the references 9R and 9L, the letter R in the references standing for "right" and the letter L for "left". Again to make things clearer, the description of this embodiment explains only the processing of measured values in connection with the measured value delivering sensors 23R and 23L and the connecting cables 9R and 9L, since the explanation would be identical for the other measured value delivering sensors 23.

In this embodiment the particular connecting cables 9R and 9L extend from the measured value delivering sensor 23R and the measured value delivering sensor 23L to an adder 97 (block "+") which forms the analog sum of the analog measured values of the measured value delivering sensors 23R and 23L. This sum is supplied to the zero balance circuit 91 (block "0"). The remainder of the processing is identical to that in the embodiment illustrated in FIG. 9, and will therefore not be repeated for FIG. 10.

In this embodiment shown in FIG. 10, therefore, for each measurement the identification of the interrogated crossbeam 6, the sum of the two measured values associated with such crossbeam and the corresponding statement of time are stored together digitally in the digital store 95. This enables the evaluating device (computer 87 in FIG. 8) to precisely determine the location, time and force for each measurement; in the embodiment shown in FIG. 10 the location determined is only the position of the crossbeam 6 in the running direction X (FIGS. 1 and 8), the force determined being only the total force exerted on the crossbeam 6, while the expense of the circuit is substantially reduced in comparison with the embodiment illustrated in FIG. 9, and the maximum cycle and measuring speeds attainable are substantially doubled.

The embodiment illustrated in FIG. 9 is therefore a variant of the invention which is preferred for the performance of a thorough investigation of the gait of the living being, while the embodiment illustrated in FIG. 10 is a variant of the embodiment which is preferred for the performance of an investigation of a rapid gait of the living being.

With the stated width of about 25 mm for the crossbeam taken by way of example, six to eight force sensing devices are acted upon by the foot of a horse, which arrangement produces a resolution in the running direction making possible an adequately precise local determination of the loadings occurring and corresponding measurements of the distance between the impingements of the different extremities of the horse. In combination with the total length of the measuring surface of about 4000 mm, this width of about 25 mm for the crossbeam provides an optimum compromise with regard to expense, interrogation speed, the space required, etc.

This optimum compromise is made possible on the one hand by the fact that only the measured value delivering sensors which experience a load are interrogated, so that in each interrogation cycle the measured values of only a part of the force sensing devices and measured value delivering sensors are processed, for instance in the case of a trotting horse usually only about 14 to 16 of a total of, for example, 160 force sensing devices, i.e.

about 28 to 32 of, for example, 320 measured value delivering sensors.

The optimum compromise is made possible on the other hand by the fact that interrogation is initiated only when a measured value for the first time exceeds a threshold value. Until then the installation is at stand-by for measuring, waiting for the first actuation of a force sensing device. Thereafter all the other force sensing devices whose measured value delivering sensors deliver a signal in excess of the threshold value are interrogated in succession, as viewed in the running direction. If in an interrogation cycle no further measured value delivering sensors acted upon are to be found, the interrogation jumps back to the start of the measured distance and cyclically again interrogates all the measured value delivering sensors acted upon. If no further measured value delivering sensors are acted upon and the maximum number of measured values (for example, 4000) has not yet been reached, interrogation waits for a limited time (for example, 2 seconds) and then terminates the measurement if no further measured value delivering sensor reports to have been acted upon.

The possibility already mentioned of adapting the measuring range by adaptation of the measuring spring is completed by the possibility of electronically controlling the amplification of the amplifier 94 in the software, with the object of making the fullest use of the operating range of the connected analog-to-digital converter 85 for the most accurate measurement possible.

The measuring results are processed and displayed in the evaluating device, for example, a computer. The two measured value delivering sensors associated with a force sensing device or its crossbeam each deliver a signal which corresponds to the force applied vertically thereto. In other words, the force exerted by the living being on a crossbeam is broken down into two components, each of which acts on one end of the crossbeam. The two components are then each broken down into a vertical part and a horizontal part. It is the vertical part which is measured by the measured value delivering sensor.

For investigating the gait of a living being, more particularly a horse, the resulting measured values are interpreted by the sum of the measured values associated with a crossbeam being formed to determine the total force exerted vertically on the crossbeam. This can be done either through the hardware in an electronic measuring system (the embodiment illustrated in FIG. 9) or by software in a computer (the embodiment illustrated in FIG. 10). To determine the location of the application of force to the crossbeam, the ratio between the difference of the two associated measured values and the their sum is formed, which operation in principle could be done by hardware in the electronic measuring system, but is preferably done by software in the computer. Of course the two measured values are equal to one another if the force is applied in the center of the crossbeam, so that in that case the aforementioned ratio is zero, while one of the measured values is zero if the force is applied adjacent the end of the crossbeam precisely above the measured value delivering sensor, so that in that case the aforementioned ratio is +1 or −1, in dependence on the end of the crossbeam which is acted upon. The aforementioned ratio therefore varies between −1 and +1 and provides a determination of the location of the application of force to the crossbeam. Software performance of this determination in a computer is familiar to an electronics engineer and will not be described in greater detail.

While the invention has been particularly shown and described with respect to the preferred embodiments thereof, it should be understood by those skilled in the art that the foregoing and other changes in form and details may be made therein without departing from the spirit and scope of the invention which should be limited only by the scope of the appended claims.

What is claimed is:

1. A method of investigating the gait of a living being having feet by measuring the force exerted by its feet on the ground and of the location, duration and course in time of the application of force in a zone of a substantially horizontal measuring surface taking the form of part of the ground, the measuring surface being subdivided substantially at right angles to the direction of movement of the living being into elongate measuring sections parallel to each other and adjacent in succession in lamellar fashion, said method comprising the steps of:
   (a) measuring the force exerted by the living being on a measuring section an dividing the force exerted into two components, one of each component acts on the measuring section adjacent a respective end thereof;
   (b) breaking the two components into a vertical and a horizontal part resulting in two horizontal parts and two vertical parts;
   (c) measuring the two vertical parts separately to obtain a measured value for each of the two vertical parts; and
   (d) cyclically interrogating the measured values in the course of an interrogation sequence corresponding to the succession of measuring sections in the direction of movement of the living being, the measured values are put into intermediate storage in an analog measured value store and subsequently compared with a predetermined threshold value, and only those measured values put into intermediate storage which exceed the threshold values are passed on for an evaluation wherein the sum of the two measured values is formed for the determination of the total force exerted vertically on the measuring section and the ratio between the difference in the two measured values and their sum is formed to determine the location where the force is exerted on the measuring section.

2. The method according to claim 1, wherein in order to determine the total force exerted vertically on a measuring section, the sum of the two measured values is formed, such sum is on the one hand put into intermediate storage and on the other hand compared with a predetermined threshold value, and only those values of the sum put into intermediate storage which exceed the threshold value are passed on for evaluation.

3. The method according to claim 2, wherein those values put into intermediate storage which exceed the threshold value are subjected to an analog-to-digital conversion, after an amplification via an analog amplifier, while a digital identification of each corresponding measured value delivering sensor and a digital statement of time are associated therewith, and each value which is being passed on for evaluation is stored together with its identification and its statement of time.

4. The method according to claim 2, wherein the cyclic interrogation sequence is initiated only on the occurrence of a value put into intermediate storage which exceeds the threshold value, and the interrogation sequence is automatically discontinued if during a predetermined period no occurrence has been detected of a value put into intermediate storage which exceeds the threshold value.

5. An apparatus for investigating the gait of a living being having feet by measuring the force exerted by its feet on the ground and of the location, duration and course in time of the application of force in a zone of a substantially horizontal measuring surface taking the form of part of the ground, said apparatus comprising:
   (a) elongate measuring sections, the measuring surface being subdivided substantially at right angles to the direction of movement of the living being into elongate measuring sections parallel to one another and adjacent in succession in lamellar fashion, the width of each of the measuring sections being smaller than the length of the foot of the living being and the length of each of the measuring sections being greater than the track width of the living being;
   (b) a plurality of measured value delivering sensors connected to an electronic evaluating unit associated with each measuring section, each of the measured value delivering sensors being a path sensor for vertical movement of a measuring spring;
   (c) a force sensing device having a substantially rectangular force sensing surface and comprising a stiff cross beam having an upper surface on which the measuring section is disposed, the cross beam borne on a lower surface thereof at opposing ends thereof, each end on a sensing block so as to act therein in the vertical direction on one of the plurality of measured value delivering sensors, the cross beam in the force sensing device mounted to move substantially only vertically and borne on a measuring spring which bears against the sensing block; and
   (d) a transmission element for the vertical movement of the measuring spring disposed between the spring and each of the plurality of measured value delivering sensors, the transmission element being operatively connected to each of the plurality of measured value delivering sensors and acted upon by a resilient means in the direction of the measuring spring.

6. The apparatus according to claim 5, wherein the measuring spring takes the form of a flat spring and is so disposed in the sensing block that its bending is limited by its coming into contact with a stationary part of the sensing block, the transmission element being substantially vertically extending and having a rod section and a tappet rod adjoining a bottom end of said rod section and a sliding member adjoining atop end of such rod section, the sliding member being guided in the vertical direction in a guide sleeve provided in the sensing block and having in an upper portion thereof a head which is engaged from below by a sealing disc bearing against the sensing block and comprises an adjusting device in which a top end thereof has a receiving depression for a bottom part of a ball whose top having a top part which bears against the measuring spring.

7. An apparatus according to claim 6 wherein there is disposed between the crossbeam and the measuring spring a ball which is trapped in a matching ball receptacle in the sensing block and is borne on the measuring spring substantially in its center, the measuring spring being mounted on two rollers which are spaced from one another and symmetrically from the center of the measuring spring and are disposed substantially parallel with one another and at right angles to the longitudinal direction of the measuring section, one roller being stationary in relation to the sensing block and the other roller being movable.

8. The apparatus according to claim 7 wherein the sensing block contains a rail strip in which the measuring spring and the ball are received and which is engaged from above in roof fashion by a U-shaped sectional strip provided on the crossbeam.

9. The apparatus according to claim 6 wherein the measured value delivering sensor comprises permanent magnets, magnetically sensitive sensor elements and attaching elements, the attaching elements being made of a resilient material and movably retaining the sensor elements and having a resilient pre-stressing which acts on the sensor elements in the direction of the tappet rod.

10. The apparatus according to claim 5, wherein the crossbeam is mounted in the force sensing device on at least one beam extending upwardly from the sensing block and is connected to such a beam via a substantially horizontal spring strap, and the force sensing device is inserted in a groove, the sensing blocks each being attached in two parallel rows to a foundation section, let into the bottom of the groove, by means of threaded bolts and clamping blocks connected to the foundation section, such clamping blocks having lugs engaging in grooves in the sensing blocks and being so disposed offset in relation to the sensing blocks that fastening screws associated with the clamping blocks are accessible to a screwdriver inserted from above between the measured value delivering sensors inserted in the sensing blocks.

11. The apparatus according to claim 10, wherein a number of force sensing devices are disposed together on an auxiliary assembly frame, the clamping blocks being connected via the attaching screws to the auxiliary assembly frame, and the latter and the individual sensing blocks being connected via the threaded bolts to the foundation section.

* * * * *